United States Patent [19]
Waldmann et al.

[11] Patent Number: 5,900,510
[45] Date of Patent: May 4, 1999

[54] PROCESS FOR THE PREPARATION OF DIAMINODIPROPYL ETHERS AND HYDROXYAMINODIPROPYL ETHERS

[75] Inventors: Helmut Waldmann, Nideggen; Klaus Nachtkamp, Düsseldorf; Josef Pedain, Köln, all of Germany; Anatoly Bazanov, St. Petersburg, Russian Federation; Alexandre Timofeev, St. Petersburg, Russian Federation; Natalja Zubritskaya, St. Petersburg, Russian Federation; Gennady Terechtchenko, St. Petersburg, Russian Federation

[73] Assignee: Bayer Aktiengesellschaft, Leverkusen, Germany

[21] Appl. No.: 08/938,881

[22] Filed: Sep. 26, 1997

[30] Foreign Application Priority Data

Oct. 4, 1996 [DE] Germany .............................. 196 40 975

[51] Int. Cl.$^6$ .................................................. C07C 209/06
[52] U.S. Cl. ............................................ 564/474; 564/480
[58] Field of Search ....................................... 564/474, 480

[56] References Cited

U.S. PATENT DOCUMENTS 3,654,370  4/1972  Yeakey ................................. 260/584 B
4,618,717  10/1986  Renken et al. ......................... 564/475

FOREIGN PATENT DOCUMENTS 434224   6/1991   European Pat. Off. .
492767   7/1992   European Pat. Off. .
619294   10/1994  European Pat. Off. .
49-29313 8/1974   Japan .

OTHER PUBLICATIONS

E.N. Yurchenko et al.: "Development of phase composition for mixed Ni–CU Chromite catalysts." Reaction Kinetics & Catalysis Letters, Bd. 44, Nr.I Jun. 1991, pp. 215–222, XP002049463.

*Primary Examiner*—Brian M. Burn
*Attorney, Agent, or Firm*—Joseph C. Gil; Lyndanne M. Whalen

[57] ABSTRACT

Diaminodipropyl ethers and hydroxyaminodipropyl ethers are prepared by catalytic amination of dipropylene glycol.

2 Claims, No Drawings

PROCESS FOR THE PREPARATION OF DIAMINODIPROPYL ETHERS AND HYDROXYAMINODIPROPYL ETHERS

BACKGROUND OF THE INVENTION

The present invention relates to a process for the preparation of diaminodipropyl ethers and hydroxyaminodipropyl ethers by catalytic amination of dipropylene glycol and to the ethers produced by this process.

U.S. Pat. No. 3,654,370 discloses a process for producing polyoxyalkylenediamines by reacting polyoxyalkylene diols with ammonia and hydrogen in the presence of a nickel catalyst. However, the polyoxyalkylene skeleton is rearranged in the course of this reaction. (cf. JP 029 313 (1974)).

SUMMARY OF THE INVENTION

It is an object of this invention to provide a process which produces diaminodipropyl ethers and hydroxyaminodipropyl ethers in good yields.

It is also an object of the present invention to provide a process for producing diaminodipropyl ethers and hydroxyaminodipropyl ethers in which the structure of the dipropylene glycol starting material is not altered by rearrangement.

It is another object of the present invention to provide diaminodipropyl ethers and hydroxyaminodipropyl ethers in which the dipropylene glycol structure has not been rearranged.

These and other objects which will be apparent to those skilled in the art are accomplished by reacting dipropylene glycol with ammonia and hydrogen in the presence of a Ni/Cu/Cr catalyst. This reaction is carried out at a temperature of from 150 to 190° C. and a pressure of from 75 to 250 bar.

DETAILED DESCRIPTION OF THE INVENTION

The present invention provides a process for the preparation of diaminodipropyl ethers and hydroxyaminodipropyl ethers in which dipropylene glycol is reacted with ammonia and hydrogen at a temperature of from 150° C. to 190° C. and at a pressure of from 75 to 250 bar in the presence of an Ni/Cu/Cr catalyst containing from 35 to 58 mol % nickel, from 10 to 30 mol % copper and from 12 to 55 mol % chromium.

The dipropylene glycol used in the practice of the present invention may be pure dipropylene glycol or any of the commercially available dipropylene glycols. An example of a suitable commercial dipropylene glycol is a mixture of the three isomers 1,1'-oxydi-2-propanol, 2-(2'-hydroxypropoxy)-1-propanol and 2,2'-oxydi-1-propanol.

The dipropylene glycol may be added to the corresponding diamines and aminoalcohols.

The reaction of dipropylene glycol with ammonia and hydrogen may be carried out in a continuous-flow reactor containing a catalyst bed at temperatures of from 150° C. to 190° C. and at a pressure of from 70 to 250 bar.

The catalyst used is preferably a mixture of nickel oxide, copper oxide and chromium oxide which has been hydrogenated and contains from 35 to 58 mol % nickel, from 10 to 30 mol % copper and from 12 to 55 mol % chromium. The catalyst is generally used in the form of a fixed bed. The catalyst may be in the form of particles of about 1 to 10 mm in size, e.g., as solid pellets. Catalysts of this type are in principle known. They are described, for example, in React. Kinet. Catal. Lett., Vol. 44, No. 1. 215–222 (1991).

As a result of the reaction of dipropylene glycol with hydrogen and ammonia, a mixture of diaminodipropyl ether and hydroxyaminodipropyl ether in a molar ratio of from 1:1.5 to 1:20 is obtained. If pure diaminodipropyl ether is the desired product, a mixture of dipropylene glycol and hydroxyaminodipropyl ether may be used as the starting material.

The products of the process of the present invention are useful intermediates for the production of plastics.

Having thus described our invention, the following Examples are given as being illustrative thereof.

EXAMPLES

Example 1

A continuous-flow reactor containing a fixed catalyst bed was used. 100 ml of a catalyst containing 55 mol % nickel, 18 mol % copper and 27 mol % chromium were placed in the reactor. The catalyst was reduced using a mixture of nitrogen and hydrogen. 100 l per hour of hydrogen (measured under normal conditions), 200 ml per hour of ammonia (liquid) and 13 ml per hour of dipropylene glycol (liquid) were then introduced into this reactor. The reaction was carried out at 170° C. and at a pressure of 200 bar. The reaction product, freed from ammonia, contained 14.3 wt. % diaminodipropyl ether, 22.1 wt. % hydroxyaminodipropyl ether, 27.4 wt. % dimethylmorpholine 15.4 wt. % water and 20.7 wt. % dipropylene glycol. The conversion of dipropylene glycol was 76.9% with a relative selectivity with regard to diaminodipropyl ether of 21.1 mol % and a relative selectivity with regard to hydroxyaminodipropyl ether of 32.4 mol %.

Pure diaminodipropyl ether (boiling point 74° C. to 75° C. at 13 mbar) and hydroxyaminodipropyl ether (boiling point 99° C. to 102° C. at 13 mbar) of more than 99 wt. % purity were obtained by rectifying distillation.

Example 2

The procedure and the catalyst were the same as those used in Example 1. 100 l per hour of hydrogen (measured under normal conditions), 200 ml per hour of ammonia (liquid) and 13 ml per hour of dipropylene glycol (liquid) were introduced into the reactor. The reaction was carried out at 150° C. and at a pressure of 200 bar. The ammonia-free reaction products obtained were as follows: 0.9 wt. % diaminodipropyl ether, 19.8 wt. % hydroxyaminodipropyl ether, 3.3 wt. % dimethylmorpholine, 4 wt. % water and 72 wt. % dipropylene glycol. The conversion of the dipropylene glycol was therefore 25.6% with a relative selectivity with regard to diaminodipropyl ether of 3.1 mol % and a relative selectivity with regard to hydroxyaminodipropyl ether of 80.5 mol %.

Example 3

The procedure was the same as that which was used in Example 1. 200 ml of a catalyst containing 38 mol % nickel, 11 mol % copper and 51 mol % chromium were placed in the reactor. This catalyst was reduced with a mixture of nitrogen and hydrogen, as in Example 1.

150 l per hour of hydrogen (measured under normal conditions), 400 ml per hour of ammonia (liquid) and 26 ml per hour of dipropylene glycol (liquid) were then introduced into the reactor. The reaction was carried out at 175° C. and at a pressure of 200 bar. The ammonia-free reaction products obtained were as follows: 10.7 wt. % diaminodipropyl ether, 26.7 wt. % hydroxyaminodipropyl ether, 26.7 wt. % dimethylmorpholine, 14.9 wt. % water and 20.9 wt. % dipropylene glycol. The conversion of the dipropylene glycol was 76.8% with a relative selectivity with regard to diaminodipropyl ether of 15.7 mol % and a relative selectivity with regard to hydroxyaminodipropyl ether of 39 mol %.

Example 4

The procedure followed and the catalyst used were the same as those used in Example 3 with the exception that a mixture of 53 wt. % dipropylene glycol and 47 wt. % hydroxyaminodipropyl ether recovered from the reaction were used as the starting material instead of dipropylene glycol. The ammonia-free reaction product obtained contained 7.6 wt. % diaminodipropyl ether, 45.9 wt. % hydroxyaminodipropyl ether, 10.6 wt. % morpholine, 5.5 wt. % water and 30.4 wt. % dipropylene glycol. The conversion of the dipropylene glycol was therefore 40.4 wt. % with a relative selectivity with regard to diaminodipropyl ether of 37.7 mol %.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the preparation of diaminodipropyl ethers and hydroxyaminodipropyl ethers comprising reacting dipropylene glycol with ammonia and hydrogen at a temperature of from 150° C. to 190° C. and at a pressure of from 75 to 250 bar in the presence of a catalyst containing from 35 to 58 mol % nickel from 10 to 30 mol % copper and from 12 to 55 mol % chromium.

2. The product of the process of claim 1 which is a mixture of diaminodipropyl ether and hydroxyaminodipropyl ether.

* * * * *